United States Patent
Gareau (10) Patent No.: US 11,134,885 B2
(45) Date of Patent: *Oct. 5, 2021

(54) QUANTITATIVE DERMOSCOPIC MELANOMA SCREENING

(71) Applicant: The Rockefeller University, New York, NY (US)

(72) Inventor: Daniel Gareau, New York, NY (US)

(73) Assignee: The Rockefeller University, New York, NY (US)

(*) Notice: Subject to any disclaimer, the term of this patent is extended or adjusted under 35 U.S.C. 154(b) by 530 days.

This patent is subject to a terminal disclaimer.

(21) Appl. No.: 15/752,081

(22) PCT Filed: Aug. 15, 2016

(86) PCT No.: PCT/US2016/047065
§ 371 (c)(1),
(2) Date: Feb. 12, 2018

(87) PCT Pub. No.: WO2017/027881
PCT Pub. Date: Feb. 16, 2017

(65) Prior Publication Data
US 2018/0235534 A1    Aug. 23, 2018

Related U.S. Application Data

(60) Provisional application No. 62/204,763, filed on Aug. 13, 2015.

(51) Int. Cl.
*A61B 5/00* (2006.01)
*G06T 7/00* (2017.01)
(Continued)

(52) U.S. Cl.
CPC ............ *A61B 5/444* (2013.01); *A61B 5/0071* (2013.01); *A61B 5/0075* (2013.01);
(Continued)

(58) Field of Classification Search
CPC ..... A61B 5/444; A61B 5/0071; A61B 5/0075; A61B 5/0077; A61B 5/7275; A61B 5/743;
(Continued)

(56) References Cited

U.S. PATENT DOCUMENTS

| 5,016,173 A | 4/1991 | Kenet et al. |
| 5,706,821 A | 1/1998 | Matcher et al. |

(Continued)

FOREIGN PATENT DOCUMENTS

| CN | 101686819 | 3/2010 |
| GB | 2502672 | 12/2013 |

(Continued)

OTHER PUBLICATIONS

International Search Report and Written Opinion for PCT Application No. PCT/US16/47065 dated Jan. 6, 2017.
(Continued)

*Primary Examiner* — Amelie R Davis
*Assistant Examiner* — John Denny Li
(74) *Attorney, Agent, or Firm* — Pearl Cohen Zedek Latzer Baratz LLP (57) ABSTRACT

A standardized, quantitative risk assessment method and apparatus for noninvasive melanoma screening. The apparatus and methods generate a melanoma Q-Score which calculates and displays a probability that a skin lesion is melanoma.

13 Claims, 4 Drawing Sheets

(51) Int. Cl.
  *G16H 50/30* (2018.01)
  *G06T 7/68* (2017.01)
  *G06K 9/62* (2006.01)
(52) U.S. Cl.
  CPC .......... *A61B 5/0077* (2013.01); *A61B 5/7275* (2013.01); *A61B 5/743* (2013.01); *G06K 9/628* (2013.01); *G06T 7/0012* (2013.01); *G06T 7/68* (2017.01); *G16H 50/30* (2018.01); *G06T 2200/36* (2013.01); *G06T 2207/10024* (2013.01); *G06T 2207/10064* (2013.01); *G06T 2207/20081* (2013.01); *G06T 2207/30088* (2013.01); *G06T 2207/30096* (2013.01)
(58) Field of Classification Search
  CPC ..... G06T 7/68; G06T 7/0012; G06T 2200/36; G06T 2207/10024; G06T 2207/10064; G06T 2207/20081; G06T 2207/30088; G06T 2207/30096; G16H 50/30; G06K 9/628
  See application file for complete search history.

(56) References Cited

U.S. PATENT DOCUMENTS

| | | | |
|---|---|---|---|
| 5,836,872 | A | 11/1998 | Kenet et al. |
| 5,944,598 | A | 8/1999 | Tong et al. |
| 6,208,749 | B1 | 3/2001 | Gutkowicz-Krusin et al. |
| 6,993,167 | B1 | 1/2006 | Skladnev et al. |
| 7,006,223 | B2 | 2/2006 | Mullani |
| 7,027,153 | B2 | 4/2006 | Mullani |
| 7,167,243 | B2 | 1/2007 | Mullani |
| 7,167,244 | B2 | 1/2007 | Mullani |
| 7,603,031 | B1 | 10/2009 | Vlaud |
| 7,894,651 | B2 | 2/2011 | Gutkowicz-Krusin et al. |
| 8,218,862 | B2 | 7/2012 | Demirti |
| 8,498,460 | B2 | 7/2013 | Patwardhan |
| 8,971,609 | B2 | 3/2015 | Gareau et al. |
| 10,182,757 | B2 | 1/2019 | Gareau et al. |
| 10,307,098 | B2 | 6/2019 | Gareau |
| 2003/0078482 | A1 | 4/2003 | Kenen |
| 2004/0267102 | A1 | 12/2004 | Skladnev |
| 2005/0228264 | A1 | 10/2005 | Grichnik |
| 2005/0232474 | A1* | 10/2005 | Wei .......................... G06T 7/11 382/128 |
| 2007/0232930 | A1 | 10/2007 | Freeman et al. |
| 2008/0123106 | A1 | 5/2008 | Zeng et al. |
| 2008/0132794 | A1 | 6/2008 | Alfano et al. |
| 2008/0214907 | A1 | 9/2008 | Gutkowicz-Krusin et al. |
| 2008/0275315 | A1 | 11/2008 | Oka et al. |
| 2009/0016491 | A1 | 1/2009 | Li |
| 2009/0174878 | A1 | 7/2009 | Wadman |
| 2009/0220415 | A1 | 9/2009 | Shachaf et al. |
| 2009/0279760 | A1 | 11/2009 | Bergman |
| 2010/0185064 | A1 | 7/2010 | Bandic |
| 2010/0255795 | A1 | 10/2010 | Rubinsky et al. |
| 2010/0271470 | A1 | 10/2010 | Stephan et al. |
| 2010/0302358 | A1 | 12/2010 | Chen |
| 2011/0013006 | A1 | 1/2011 | Uzenbajakava et al. |
| 2012/0041284 | A1 | 2/2012 | Krishnan et al. |
| 2012/0041285 | A1 | 2/2012 | Krishnan et al. |
| 2012/0071764 | A1 | 3/2012 | Yaroslavsky et al. |
| 2012/0170828 | A1 | 7/2012 | Gareau et al. |
| 2012/0172685 | A1 | 7/2012 | Gilbert |
| 2012/0259229 | A1 | 10/2012 | Wang |
| 2012/0320340 | A1 | 12/2012 | Coleman, III |
| 2013/0014868 | A1 | 1/2013 | Ishida |
| 2013/0053701 | A1 | 2/2013 | Wiest et al. |
| 2013/0108981 | A1 | 5/2013 | Duret |
| 2013/0114868 | A1 | 5/2013 | Burlina et al. |
| 2013/0116538 | A1 | 5/2013 | Herzog et al. |
| 2014/0036054 | A1 | 2/2014 | Zouridakis |
| 2014/0213909 | A1 | 7/2014 | Mestha |
| 2014/0350395 | A1* | 11/2014 | Shachaf ............... A61B 5/0082 600/431 |
| 2015/0025343 | A1 | 1/2015 | Gareau et al. |
| 2015/0082498 | A1 | 3/2015 | Meyer |
| 2016/0199665 | A1* | 7/2016 | Gardiner ................ A61B 5/445 607/88 |
| 2017/0205344 | A1 | 7/2017 | Gemp et al. |

FOREIGN PATENT DOCUMENTS

| | | |
|---|---|---|
| JP | 2005111260 | 9/2004 |
| JP | 2005192944 | 5/2005 |
| JP | 2005192944 | 7/2005 |
| JP | 2006-074259 | 3/2006 |
| JP | 2006074259 | 3/2006 |
| JP | 2007511243 T | 5/2007 |
| JP | 2010520774 T | 6/2010 |
| JP | 2013514520 T | 4/2013 |
| WO | WO 90/13091 | 11/1990 |
| WO | WO2006078902 | 7/2006 |
| WO | WO 2011/087807 | 7/2011 |
| WO | WO2011112559 | 9/2011 |
| WO | WO2011112559 | 1/2012 |
| WO | WO 2012/162596 | 11/2012 |
| WO | WO2015/013288 | 1/2015 |
| WO | WO2017053609 | 3/2017 |
| WO | WO2020/146489 | 7/2020 |
| WO | WO 2020/146489 | 7/2020 |

OTHER PUBLICATIONS

Nehal, Kishwer et al., Skin imaging with reflectance confocal microscopy, Seminars in Cutaneous Medicine and Surgery, 2008, 27:37-43.

"Melanoma." Skin Cancer. Skin Cancer Foundation, n.d. Web. Jul. 29, 2013. <http://www.skincancer.org/skin-cancer-information/melanoma>.

Busam, Klaus J., Ashfaq A. Marghoob, and Allan Halpern. "Melanoma Diagnosis by Confocal Microscopy: Promise and Pitfalls." Journal of Investigative Dermatology. 125.3 (2005):n. p. Print.

Gareau, Daniel S., Glenn Merlino, Christopher Corless, Molly Kulesz-Martin, and Steven L. Jacques. "Noninvasive Imaging of Melanoma with Reflectance Mode Confocal Scanning Laser Microscopy in a Murine Model." Journal of Investigative Dermatology. (2007): n. p. Print.

Gareau, Dan. "Automated identification of epidermal keratinocytes in reflectance confocal microscopy." Journal of Biomedical Optics. 16.3 (2011): n. p. Print.

Gareau, Dan, Ricky Hennessy, Eric Wan, Giovanni Pellacani, and Steven L. Jacques. "Automated detection of malignant features in confocal microscopy on superficial spreading melanoma versus nevi." Journal of Biomedical Optics. 15.6 (2010): n. p. Print.

Argenziano, G. et al., Dermoscopy improves accuracy of primary care physicians to triage lesions suggestive of skin cancer. J Clin Oncol, 2006. 24(12): p. 1877-82.

Artificial intelligence—how far can it go in dermatology? Modernizing Medicine Jul. 12, 2016; Available from: https://www.modmed.com/artificial-intelligence-how-far-can-it-go-in-dermatology/.

Breiman, L., Random Forests. Machine Learning, 45, 2001 Kluwer Academic Publishers. 5-32.

Cortes, C. and V. Vapnik, Support-vector networks. Machine Learning, 1995. 20(3): p. 273-297.

Doyle-Lindrud, S., Watson will see you now: a supercomputer to help clinicians make informed treatment decisions. Clin J Oncol Nurs, 2015.19(1): p. 31-2.

Drugge, R.J., et al., Melanoma screening with serial whole body photographic change detect/on using Melanoscan technology. Dermatol Online J, 2009. 15(6): p. 1.

Elder, D.E., Dysplastic naevi: an update. Histopathology, 2010. 56(1): p. 112-20.

Emery, J.D., et al., Accuracy of SIAscopy for pigmented skin lesions encountered in primary care: development and validation of a new diagnostic algorithm. BMC Dermatol, 2010. 10: p. 9.

Fisher, R.A., The use of multiple measurements in taxonomic problems. Annals of Eugenics, 1936.7: p. 179-188.

(56) References Cited

OTHER PUBLICATIONS

Fix, E. and J.L. Hodges, Discriminatory Analysis, nonparametric discrimination: Consistency properties. 1951.
Friedman, J.H., Multivariate Adaptive Regression Splines. The Annals of Statistics, 1991, 19(1): p. 1-67.
Friedman, J., T. Hastie, and R. Tibshirani, Regularization Paths for Generalized Linear Models via Coordinate Descent. Journal of Statistical Software, 2010. 33(1): 1-22.
Friedman, Robert J., et al., The Diagnostic Performance of Expert Dermoscopists vs a Computer-Vision System on Small-Diameter Melanomas, Arch Dermatol. 2008;144(4):476-482.
Henning, J. Scott, et al., The CASH (color, architecture, symmetry, and homogeneity) algorithm for dermoscopy, J Am Acad Dermatol 2007;56:45-52.
Hofner, B., et al., Model-based boosting in R: a hands-on tutorial using the R package mboost. Computational Statistics, 2012. 29(1-2): p. 3-35.
IBM detects skin cancer more quickly with visual machine learning. Computer World News; Available from: http://www.computerworld.com/article/2860758/ibm-detects-skin-cancer-more-quickly-with-visual-machine-learning.html.
Malvehy, J., et al., Clinical performance of the Nevisense system in cutaneous melanoma detection: an international, multicentre, prospective and blinded clinical trial on efficacy and safety. Br J Dermatol, 2014. 171 (5): p. 1099-107.
Memorial Sloan Kettering Trains IBM Watson to Help Doctors Make Better Cancer Treatment Choice 2014; Available from: https://www.mskcc.org/blog/msk-trains-ibm-watson-help-doctors-make-better-treatment-choices.
Menzies, S.W., et al., The performance of SolarScan: an automated dermoscopy image analysis instrument for the diagnosis of primary melanoma. Arch Dermatol, 2005. 141 (11): p. 1388-96.
Monheit G., et al., The performance of MelaFind: a prospective multicenter study. Arch Dermatol, 2011. 147(2): p. 188-94.
Nachbar, F., et al., The ABCD rule of dermatoscopy. High prospective value in the diagnosis of doubtful melanocytic skin lesions. J Am Acad Dermatol, 1994.30(4): p. 551-9.
Otsu, N., A threshold selection method from gray-level histogram. IEEE Transactions on System Man Cybernetics., 1979. SMC-9(1): p. 62-66.
Ramezani, M., et al., Automatic Detection of Malignant Melanoma using Macroscopic Images. J Med Signals Sens, 2014.4(4): p. 281-90.
Rigel, D.S., et al., The evolution of melanoma diagnosis: 25 years beyond the ABCDs. CA Cancer J Clin, 2010. 60 (5): p. 301-16.
Rokach, L., Ensemble-based classifiers. Artificial Intelligence Review, 2010. 33: p. 1-39.
Rosipal, R. et al., Overview and Recent Advances in Partial Least Squares, in Subspace, Latent Structure and Feature Selection, C. Saunders, et al., Editors. 2006, Springer Berlin Heidelberg. p. 34-51.
Sgouros, D., et al., Assessment of SIAscopy in the triage of suspicious skin tumours. Skin Res Technol, 2014; 0:1-5.
Vestergaard, M,E., et al., Dermoscopy compared with naked eye examination for the diagnosis of primary melanoma: a meta-analysis of studies performed in a clinical setting, British Journal of Dermatology 2008 159, pp. 669-676.
Wolf, J A et al., Diagnostic inaccuracy of smartphone applications for melanoma detection—reply. JAMA Dermatol, 2013.149(4): p. 422-426.
Office Action for Chinese patent application No. CN201480052009. 5.
Office Action for Japanese patent application No. 2016-529829 dated May 22, 2018.
Masood et al., Computer aided diagnostic support system for skin cancer. a review of techniques and algorithms. Int J Biomed Imaging, Dec. 23, 2013, vol. 2013, No. 323268, p. 1-22.
Hosking et al. Hyperspectral imaging in automated digital dermoscopy screening for melanoma. Lasers Surg Med. Mar. 2019, published online Jan. 17, 2019), vol. 51, No. 3, p. 241-222.

\* cited by examiner

QUANTITATIVE DERMOSCOPIC MELANOMA SCREENING

CROSS-REFERENCE TO RELATED APPLICATIONS

This application is a United States National Phase Application of PCT International Application No. PCT/US16/47065, filed Aug. 15, 2016, claiming benefit of U.S. Provisional Patent Application No. 62/204,763, filed Aug. 13, 2015, which are incorporated by reference.

BACKGROUND OF THE INVENTION

The invention is directed to detection of skin disease from image analysis of a skin lesion.

Melanoma, the most lethal skin cancer, incurs immense human and financial cost. Early detection is critical to prevent metastasis by removal of primary tumors. The early lateral growth phase is a vastly preferable detection window to the subsequent phase of metastatic initiation. Optical detection technologies for automated quantitative metrics of malignancy are needed to more accurately guide decisions regarding the need to biopsy and to make preoperative determination of adequate margins for surgical excision. After invasive biopsy or excision, diagnosis obtained by histopathologic evaluation is nearly 100% accurate; however, deciding which lesions to biopsy is challenging. Only 3% to 25% of surgically-excised pigmented lesions are diagnosed as melanomas. Hence there is a need for noninvasive screening mechanisms that are both widespread and more accurate.

A dermatoscope typically consists of a light emitting diode (LED) illuminator, a low magnification microscope, and a clear window surface to flatten the skin against. The use of polarization enables partial rejection of deeply penetrating light, which can enhance superficial features of particular diagnostic interest. A digital imaging camera may also be attached to the dermatoscope. Dermatologists use dermatoscopes to make the screening determination, but better diagnostics are needed to guide early surgical intervention. The present invention leverages previous pattern recognition approaches as well as a robust machine learning method to yield a quantitative diagnostic metric, the melanoma Q-score, for noninvasive melanoma screening.

U.S. patent application Ser. No. 14/051,053 (Patent Application Publication 2015/0025343), filed Oct. 10, 2013, and Ser. No. 14/907,208 (Patent Application Publication 2016/0166194), having an international filing date of Jul. 22, 2014, by the applicant herein, which are incorporated by reference in their entirety, describe methods and apparatus for obtaining a diagnosis of skin disease in a lesion on a subject's skin from a dermoscopic image of the lesion. These patent applications generally describe obtaining image data from the lesion, transforming the image data into polar coordinates and processing the image data using a clock-like sweep algorithm to obtain metrics and/or one or more classifiers defining the rotational symmetry of a lesion on the subject's skin to produce an indication of the likelihood of the presence or absence of skin disease in the subject. It is desirable to improve these methods and apparatus for more accurate melanoma screening.

SUMMARY OF THE INVENTION

One of the objects of the present invention is to employ algorithms that perform evaluations of image data obtained from reflected or fluoresced light from skin lesions with greater sensitivity, specificity and overall diagnostic accuracy, and which can be used to produce diagnostically relevant quantitative imaging biomarkers.

Another object of the invention is to combine a dermatoscope, digital camera and automated screening by computer vision to bridge the diagnostic accuracy gap between invasive and noninvasive pathological analyses.

In one aspect, the invention is an apparatus for detecting skin disease in a lesion on a subject's skin, comprising: a mechanical fixture having a flat surface to position or press against the subject's skin to define a distal imaging plane containing said lesion; a camera adapted to obtain image data from the lesion; a processor adapted to process the image data with a clock-like sweep algorithm to obtain metrics and/or one or more classifiers defining the rotational symmetry of the pigmented lesion; and an output device that indicates a likelihood of the presence or absence of skin disease in the subject obtained from the metrics and/or one or more classifiers. In this context, "metrics and/or one or more classifiers" means the likelihood may be obtained from metrics, from one or more classifiers or from a combination of metrics and one or more classifiers.

The clock-like sweep algorithm, for example, evaluates the brightness of pixels on a line segment between the center of the lesion image and the lesion image border as the line segment rotates around the center of the lesion with one end of the line segment fixed at the center of the lesion image. Rotational symmetry refers to different information obtained on the line segment at different angular positions. Such information may be directly related to the image, such as the image brightness, or may be information indirectly related to the image such as the average pigmented network branch length for the pigmented network branches encountered by a line segment. In the case of indirect information, pre-processing of the image is completed to define such information for each part of the image. Continuing the example, a circle with uniform brightness throughout exhibits perfect rotational symmetry. However, if the distance from the border of the lesion to the center of the lesion is different at different angular positions, or if the brightness of pixels differs at different positions on the line segment, or at different angular positions of the line segment, then the lesion is not rotationally symmetric, but asymmetric. This asymmetry may be quantified and used to produce diagnostically relevant metrics and/or one or more classifiers.

According to embodiments of the invention, a classifier function used to arrive at a Q-score includes at least the total number of colors in a lesion (MC1), and further includes at least one additional imaging biomarker selected from the group consisting of: normalized difference in lesion size between the red and blue color channels (MC2); mean coefficient of variation of lesion radii among the color channels (MC3); binary presence of blue-gray or white in the image (MC4); average of the absolute value of the derivative of $R_m(\theta)$ over the angular sweep is the mean instantaneous brightness shift from one angular analysis position to the next over the entire 360-degree angular range (B1); variance over the angular sweep of the variance in pixel brightness over the radial sampling arm (B2); mean error between a model $s_e(r)$ and image data $p_e(r)$ evaluated over a range equal to the distance between the center and the lesion border but centered on the edge of the lesion (B3); mode error in the blue channel (B4); standard deviation of the set of derivative values of the mean brightness (B5); normalized inter-branch pixel intensity variation (B8); standard deviation of error (B9); normalized angular coefficient of brightness variation (B10); standardized variance of branch lengths (B11); normalized range of angular brightness (B12); mean intra-branch coefficient of variation (B15); standard deviation of sigmoidal edge fit slope values (R1); fractal dimension of the lesion segment binary image (R2); connectedness of the pigmented network (R3); size of the lesion segment (R4); mean slope for an edge fit function $s_e(r)$ (R5); coefficient of variation in the lesion radius over the angular sweep (R6); range in number of branches detected as a function of angle (R7); range in a standard deviation of pixel brightness on the angular sweep arm over the angular sweep (R8); coefficient of variation in pixel brightness within the lesion (R9); mode error in the red channel (R10); maximum asymmetry of the lesion silhouette (R11); sum of the normalized derivative in lesion radius D over the angular sweep (R12); and asymmetry of the lesion silhouette (R13).

These and other aspects of the invention are shown and described below.

DETAILED DESCRIPTION OF THE INVENTION

One embodiment of the present invention is directed to a system including a camera, a mechanical fixture for illuminating the subject's skin and positioning the camera fixedly against the subject's skin, at least one processor adapted to perform the clock sweep algorithm, and at least one output device to display diagnostic information.

The camera is preferably a digital camera and may include a charged coupled device (CCD) sensor or complementary metal oxide semiconductor (CMOS), as known in the art. The camera may be a commercially available portable camera with an integrated illumination system or flash and a sensor array detecting Red Green and Blue (RGB) light. Alternatively an external illumination system may be provided and the camera sensor array may be adapted to receive "hyperspectral" light, meaning light divided into more spectral wavelength bands than the conventional RGB bands, which may be in both the visible and non-visible range. Details concerning operable illumination systems and hyperspectral imaging are provided in more detail in the aforesaid Patent Application Publication 2015/0025343 by the applicant herein and incorporated by reference.

In embodiments, the camera acquiring the image data according to the invention is adapted to obtain images from light fluoresced from the surface of the lesion. The use of fluoresced light is unexpected in this context because it is not as strong as reflected light, but there may be some advantages in some contexts. For this purpose, specific or non-specific targets in the lesion may be labeled with a fluorescent label to improve the ability to obtain the image data.

For the samples described in the present application, non-polarized dermoscopy images were acquired with an EpiFlash™ (Canfield Inc., NJ) dermatoscope attached to a Nikon™ D80 camera.

Data obtained from the lesion image is processed into "imaging biomarkers" or "melanomas imaging biomarkers" (MIBs), which is a preferred term for what have conventionally been referred to as "metrics". The methods of the invention leverage some 33 predictive MIBs in producing a "Q-Score" indication of the likelihood that a suspected lesion is melanoma. A conventional computer having a processor and memory may be used for performing the data processing operations described herein, and the processor may be local and onboard the camera or other image acquisition apparatus, or the processor may be located remotely.

For 120 patients who underwent biopsy or surgical excision of their suspicious lesion, the methods herein were used to predict the biopsy diagnosis (melanoma or nevus) using only the dermoscopy image that was taken of the lesion before biopsy. Performing these methods on samples that had already been biopsied provided a measure of the predictive ability of the apparatus and method of the invention when applied to a lesion on a subject's skin. The methods and apparatus are adapted to provide a Q-score for a lesion while it is still on a subject's skin.

In the study, at a clinically reasonable 98% sensitivity, three of the Q-score formulations achieved 17%, 28% and 38% specificities, which are considerably higher than the se/sp=98%/10% of current practice. A melanoma Q-score, the quantitative probability of melanoma, was generated by an algorithm, drawing on the image processing and machine learning fields. Producing the Q-score algorithm includes a two-step process: (1) discrete quantitative imaging biomarkers were derived from the images that targeted specific diagnostic features and then (2) the metrics were evaluated to combine them in a function (one or more classifiers) with maximized diagnostic precision.

In the first step, two types of metrics were extracted from the images: a set of 36 single-color-channel (SCC) metrics that were extracted from single color channels and a set of 7 Multi-Color (MC) that were extracted from the RGB color channel triad by characterizing differences in lesion features between the RGB color channels. Three versions of each SCC metric were extracted for each lesion, one extracted from each color channel. Among the MC metrics were both the most and least statistically significant descriminators of melanoma vs. nevus ($p=9\times10^{-7}$ for MC1 and $p=0.901$ for MC7) and among the SCC metrics, there emerged a naturally occurring mutual exclusivity of metric significance in the red and blue channels. The full set of 43 metrics was filtered by excluding 12 insignificant ($p>0.05$) metrics using univariate two-tailed unpaired t-tests for continuous variables and Fisher Exact Test for categorical ones.

In the second step, the remaining 31 metrics, 4 MC and 27 SCC where the color channel version (for example blue or red) with maximum significance was used, was input to twelve different statistical/machine learning methods, known in the art, for example from Kuncheva, L., Combining Pattern Classifiers, Methods and Algorithms (Wiley 2014). Each method output a melanoma likelihood for each lesion. Then the likelihoods produced by all methods were combined into the ultimate best estimate of the probability of melanoma, the melanoma Q-score. This method of "training" an algorithm may be used with a training set of lesions of known pathology.

An ensemble of classifiers generates more accurate predictions than a single classifier. Thus, according to embodiments, a melanoma Q-Score is obtained by evaluating the median probability across K available classifiers.

$$Q_{score} = \text{median}\{Prob_i(\text{Melanoma}|M)\}; i=1,2,\ldots,k \quad (37)$$

Where $Prob_i \in \{(0,1)\}$ is the probability of the lesion being a melanoma, as predicted by the i-th classifier based on a set of MIBs M.

Table 1 lists classification algorithms that may be applied to melanoma discrimination according to embodiments of the invention.

TABLE 1

| Method | Description |
| --- | --- |
| NNET | Feed-forward neural networks with a single hidden layer |
| SVM (linear and Radial) | Support Vector Machines |
| GLM | Logistic regression within the framework of Generalized Linear Models |
| GLMnet | Logistic regression with the elastic-net penalization |
| GLMboost | Logistic regression with gradient boosting |
| RF | Random Forests |
| RP | CART (Classification and Regression Trees) algorithm for classification problems |
| KNN | K-nearest neighbors algorithm developed for classification |
| MARS | Multiple Adaptive Regression Splines |
| C50 | C5.0 decision tree algorithm for classification problems |
| PLS | Partial Least Squares |
| LDA | Linear Discriminant Analysis |

Images were cropped where possible to exclude artificial pen markings and scale bars commonly used in the clinic and, for lesions that were small, to exclude large areas of surrounding normal skin such that the area of lesion and normal skin were comparable. The algorithm then operated independently on each color channel of the Red/Green/Blue (RGB) image, and performed a segmentation to determine the border of the lesion in each channel. Segmentation methods known in the art may be applied for border determination, including but not limited to Otsu's method.

Figure 1:
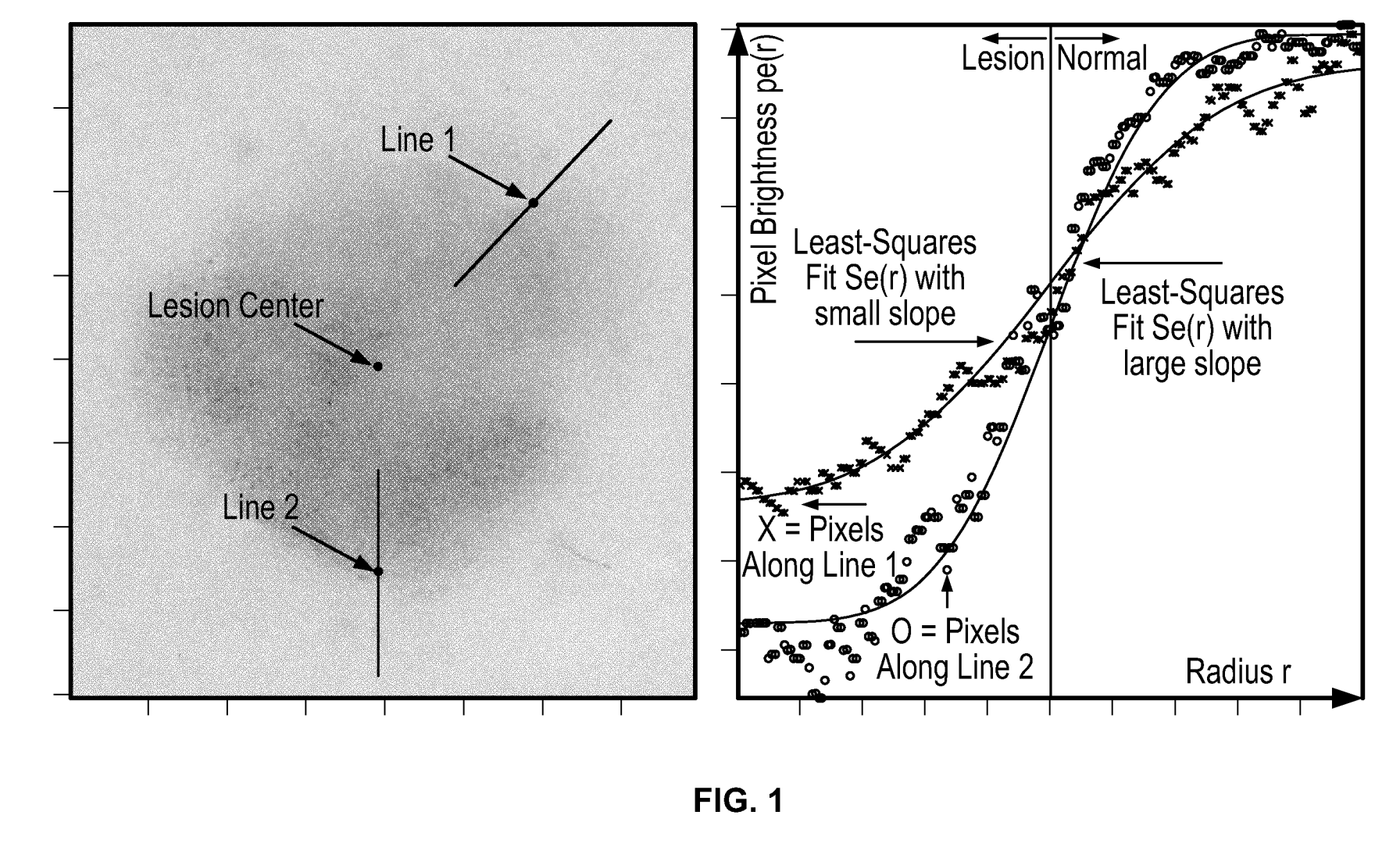
FIG. 1 depicts fitting for edge demarcation of a lesion according to an embodiment of the invention.

FIG. 1 depicts fitting for edge demarcation, quantified as the slope of the transitioning from dark pixels inside the lesion to bright pixels outside the lesion. Increased slope of the fitting mathematical function resulted from increased lesion border demarcation. The two radial lines (Line 1, Line 2) drawn on the lesion include the lesion border from inside the lesion where the pixels are dark to outside the lesion where the pixels are bright in normal skin illustrate two locations where the demarcation is gradual (Line 1) and sharp (Line 2). The pixel brightness data points extracted along these two lines (x for Line 1 and o for Line 2), $p_e(r)$, was fit to a mathematical model, $s_e(r)$, to yield the fitting parameters, which were used to produce Melanoma Imaging Biomarkers marked "Border" in FIG. 2. This includes the edge demarcation slope, which is the slope of the solid line at the lesion border between normal skin and lesion and the error in the fit, which is the sum of the squared differences between the data points, $p_e(r)$ and the error function fit, $s_e(r)$. Melanomas had a sharper border, a higher degree in variability of border sharpness and a greater fitting error.

An important aspect of the overall image processing routine was the analysis of angular variation in the lesion properties. Properties ranging from (simple) the gray-scale brightness to (complex) the average pigmented network branch length were evaluated along a line that connected the geometric center of the lesion segment and a point on the lesion border as that line rotated in an angular sweep about the lesion. The total range of angular variation in brightness, which is calculated by subtracting the minimum brightness from the maximum brightness, is a single number that is larger for rotationally irregular lesion such as a melanoma. The dermoscopic criteria that increase this metric are irregularities of pigment distribution in a lesion including, atypical network, atypical globules, off center blotches, peripheral tan structure-less areas and regression structures. For each of the three RGB color channels in each image, a set of metrics was derived based on the pixel gray-scale values. Additional metrics were derived from variation between the gray-scale values in the separate color channel images and also derived from variations in the metrics derived from the various color channel data. The metric described above and illustrated was produced for each of 3 channels per dermoscopic image by being analyzed on each of the red, green and blue color channel-images. Similarly, 26 other metrics extracted from single color channels were statistically different (p<0.05) for melanomas versus nevi. Four additional statistically significant metrics used information from all color channels. Mathematical formulae for each of the significant (p<0.05) metrics are described below. In a few instances, the algorithm failed to produce a result. The limitations of the algorithm were 1) the inability of the algorithm to converge on a lesion border in 6.7% of the cases due to hair, lesion segments that extended beyond the image border and 2) non-automated tasks: cropping of the lesion and choice of sample dermoscopic colors in the data set.

The most discriminative metric was the total number of colors in the lesion ("MC1"), with a p-value=$9 \times 10^{-7}$, as identified by a simplified colorimetry approach that classified each pixel in the image as potentially one of 6 dermoscopic colors. Table 2 below shows mean ratios for intensities between color channel pairs. These values are the empirical color channel ratios for manually selected regions in the test set blind to the gold standard diagnosis. These were the input values for the MC1 Melanoma Imaging Biomarker, which evaluated pixels for the presence of colors.

TABLE 2

| Color | R/B | R/G | B/G |
| --- | --- | --- | --- |
| dark brown | 1.90 ± 0.43 | 2.02 ± 0.40 | 1.07 ± 0.22 |
| light brown | 1.72 ± 0.46 | 1.62 ± 0.26 | 0.94 ± 0.14 |
| Black | 0.46 ± 0.55 | 0.75 ± 0.64 | 1.74 ± 1.18 |
| Red | 1.81 ± 0.69 | 1.98 ± 0.61 | 1.10 ± 0.28 |
| blue-gray | 1.26 ± 0.34 | 1.32 ± 0.25 | 1.05 ± 0.13 |
| White | 0.92 ± 0.10 | 1.2008 ± 0.09 | 1.30 ± 0.08 |

If the pixel ratio of red to blue (R/B) was within one standard deviation of the mean for that color, and the same was true for R/G and B/G, than the pixel was assigned that color. For each pixel, a sequential check was made for the presence of colors in the order [light brown, dark brown, black, red, blue-gray and white]. In this manner, the two most common colors [light brown, dark brown], were first identified as the least suspicious group. Next, red black and red were identified as more suspicious. Blue-gray and white were identified as most suspicious. The algorithm checked each pixel for each color, leaving the assignment of the last checked (most suspicious) color as the designated color for that pixel. Finally, a color vector (CV) was produced indicating the presence or absence of each color. For instance CV=[1 1 1 0 0] would result from a dermoscopic image where the lesion contained light brown, dark brown and red but no black or blue-gray/white.

MC1 is the number of dermoscopic colors identified in the lesion, defined as follows:

$$MC1 = \sum_{i=1}^{5} CL(i) \qquad (1)$$

Let L(y,x) denote an image mask of the lesion segment with value 1 inside the lesion and value 0 outside the lesion. Let $L_{red}(y, x)$, $L_{green}(y, x)$ and $L_{blue}(y, x)$ be masks derived from the red, green and blue channels of the color image, respectively. MC2 is then the normalized difference in lesion size between the red and blue color channels:

$$MC2 = \frac{\sum_{x=1}^{Nx}\sum_{y=1}^{Ny} L_{red}(y, x) - \sum_{x=1}^{Nx}\sum_{y=1}^{Ny} L_{blue}(y, x)}{\sum_{x=1}^{Nx}\sum_{y=1}^{Ny} L_{red}(y, x)} \qquad (2)$$

Let $R(\theta)$ be the length of the radial between the geometric center of the lesion and a point on the lesion border that sweeps over the angle $\theta$ from $\theta=0$ to $\theta=2\pi$ radians. Let $R_R(\theta)$, $R_G(\theta)$ and $R_B(\theta)$ be three versions where the geometric centers and the borders are those extracted from $L_{red}(y, x)$, $L_{green}(y, x)$ and $L_{blue}(y, x)$, respectively.

$$R_{var}(\theta) = \frac{\sigma(R_R(\theta), R_G(\theta), R_B(\theta))}{\langle R_R(\theta), R_G(\theta), R_B(\theta)\rangle} \qquad (3)$$

MC3 is then the mean coefficient of variation of lesion radii among the color channels, where $\langle\rangle$ denotes the expectation value or mean operator.

$$MC3 = \langle R_{var}(\theta)\rangle|_{\theta=0}^{\theta=2\pi} \qquad (4)$$

where, as an illustration of the definition of the mean value, for a set x that contains n elements:

$$\langle x\rangle = \frac{\sum_{i=1}^{n} x_i}{n} \qquad (5)$$

MC4 is the binary presence of blue-gray or white in the image.

$$MC4 = CL(5) \qquad (6)$$

Let $p(r_1)$ be the pixel brightness along a radial line $r_1$ connecting the center point of the lesion and a point on the peripheral edge of the lesion. Let $R_m(\theta)$ be the mean pixel brightness $\langle p(r_1)\rangle$ along a set of lines that vary as specified by the angle $\theta$. As $\theta$ varies in increments of $d\theta$ one full rotation from zero to $2\pi$ radians (360 degrees), the set of lines $r_1$ sweep the lesion like a clock arm sweeping an analog clock.

$$R_m(\theta) = \langle p(r_1)\rangle|_{\theta=0}^{\theta=2\pi} \qquad (7)$$

$$R_{std}(\theta) = \sigma(p(r_1))|_{\theta=0}^{\theta=2\pi} \qquad (8)$$

where, an illustration of the definition of the standard deviation, for a set x that contains n elements:

$$\sigma(x) = \left(\frac{1}{n-1}\sum_{i=1}^{i=n}(x_i - \langle x\rangle)^2\right)^{\frac{1}{2}} \qquad (9)$$

B1 is then the average of the absolute value of the derivative of $R_m(\theta)$ over the angular sweep is the mean instantaneous brightness shift from one angular analysis position to the next over the entire 360-degree angular range.

$$B1 = \langle(|R_m(\theta_n) - R_m(\theta_{n+1})|)\rangle_{\theta=0}^{\theta=2\pi} \qquad (10)$$

B2 is the variance over the angular sweep of the variance in pixel brightness over the radial sampling arm. This variable is increased when there are some angles at which the lesion contains even pigmentation but others that contain variable pigmentation such as in reticular or globular patterns of bright and dark areas.

$$B2 = \sigma(R_{std}(\theta))|_{\theta=0}^{\theta=2\pi} \qquad (11)$$

Let $p_e(r_2)$ be the pixel brightness along a second radial line $r_2$ of the same length as $r_2$ and at the same angular sweep angle $\theta$ but extending from half-to-1.5 times the lesions radius $R(\theta)$ instead of 0-to-1 such as to be centered on the border between lesion and normal skin. $p_e(r)$ has the characteristic that half of its pixels (within the lesion) are darker than the other half of its pixels (outside the lesion). Let $s_e(r)$ be a mathematical model error function across the lesion border with three fitting parameters: Min, Max and Slope that are iteratively adjusted to minimize the least squares difference between $p_e(r)$, the data and $s_e(r)$ (FIG. S5). erf(x) is defined as twice the integral of the Gaussian distribution with 0 mean and variance of ½, as shown below with the dummy variable t. Considering $r_b$ as the lesion border pixel with approximately the mean pixel brightness in $p_e(r)$ and exactly the mean brightness of $s_e(r)$, $s_e(r)$ is defined as:

$$\text{erf}(x) = f_e(r)s_e(r) = \qquad (12)$$
$$\text{Min} + \left(f_e(r) - \frac{2}{\sqrt{\pi}}\int_0^x e^{-t^2} dt \, \text{erf}\left(\frac{r - r_b}{\text{Slope}}\right)\min(f_e(r))\right) \times \text{Max}$$

B3 is then:

$$B3 = \left(\sum_{R=0.5D}^{R=1.5D}(p_e(r) - s_e(r))^2\right)\bigg|_{\theta=0}^{\theta=2\pi} \qquad (13)$$

This error measurement is high if the lesion brightness smoothly transitions between dark inside the lesion and bright outside the lesion. The fitting algorithm, fminsearch( ) in Matlab (Mathworks Inc., Natick Mass.), was limited to 200 fitting iterations. If convergence was reached before the 200-iteration limit, the result was flagged as one type while fits that were cut off at the 200-iteration limit were flagged as a second type. B3 included only results of the second type, that did not converge by the time the iteration limit was reached.

B4 Is the mode error, calculated the same as B3 but with the mode( ) operator instead of the mean $\langle\rangle$ operator calculated for only the data that exceeded the number (200) of fitting iterations allowed.

$$B4 = \text{mode}\left(\sum_{R=0.5D}^{R=1.5D}(P_e(r) - \text{erf}(r))^2\right)\bigg|_{\theta=0}^{\theta=2\pi} \qquad (14)$$

B5 is the standard deviation of the set of derivative values of the mean brightness. The variance of the derivative of brightness describes how much variability in the instantaneous change in brightness there is over the angular sweep. If some angular ranges are flat (low intra-range brightness derivative) and some ranges vary wildly, this variable will have a high value.

$$B5 = \sigma\left(\frac{dR_m}{d\theta}\right) = \sigma(|R_m(\theta_n) - R_m(\theta_{n+1})|)|_{\theta=0}^{\theta=2\pi} \quad (15)$$

B6 was calculated like B3 except that it used all data and was not restricted to the data requiring more fitting iterations than Matlab was allowed to execute. Similarly, B7 used only the fits that did not require more iterations than (200) the maximum number of fitting iterations allowed.

A watershed analysis was developed to identify pigmented network branches. First, gray-scale images extracted from individual channels were passed through a rank filter which reset the gray-scale value of each pixel to the rank in brightness of the pixel under consideration with its group of neighboring pixels. This step was needed prior to the watershed analysis to act as a high-pass spatial filter and eliminate overall brightness variations in the lesion, leaving the local variations such as those caused by pigmented networks to be identified by the watershed analysis. Branches, which were skeletonized to a single pixel width down their spine, were characterized by three features: their length, their mean brightness and their angle with respect to the lesion centroid. The MR clock sweep scored the mean pixel intensity of the branches $I_{branch}(\theta)$, the standard deviation of intra-branch pixel intensity variation $\sigma_{branch}$, the mean length of the branches $L_{branch}(\theta)$ and the total number of branches $N_{branch}(\theta)$ within a differential angle element that traced with the clock MR clock sweep. B8 is then the normalized inter-branch pixel intensity variation.

$$B8 = \frac{\sigma(I_{branch}(\theta)|_{\theta=0}^{\theta=2\pi})}{\langle I_{branch}(\theta)|_{\theta=0}^{\theta=2\pi}\rangle} \quad (16)$$

B9 Is the standard deviation of the error measurement like in B3, except that the standard deviation operator σ is used instead of the mean < > operator. B9 was evaluated only for fits requiring more fitting iterations than the 200 iterations allowed.

$$B9 = \sigma\left(\sum_{R=0.5D}^{R=1.5D}(P_e(r) - \text{erf}(r))^2\right)\Big|_{\theta=0}^{\theta=2\pi} \quad (17)$$

B10 is the normalized angular coefficient of brightness variation.

$$B10 = \frac{\sigma(R_m(\theta))}{\langle R_m(\theta)\rangle} \quad (18)$$

B11 The standardized variance of branch lengths.

$$B11 = \frac{\sigma(L_{branch})|_{\theta=0}^{\theta=2\pi}}{\langle L_{branch}|_{\theta=0}^{\theta=2\pi}\rangle} \quad (19)$$

B12 is the normalized range of angular brightness.

$$B12 = \frac{\max(R_m(\theta)) - \min(R_m(\theta))}{\langle R_m(\theta)\rangle} \quad (20)$$

B13 is calculated B6 except the standard deviation operator σ is used instead of the mean < > operator. Like B6, B13 used all the data.

$$B13 = \sigma\left(\sum_{R=0.5D}^{R=1.5D}(P_e(r) - \text{erf}(r))^2\right)\Big|_{\theta=0}^{\theta=2\pi} \quad (21)$$

B14 Is the standard deviation σ( ) of the error measurement as in B13 except that B14 was evaluated only for the fits that completed within the allowed number (200) of fitting iterations.

Let $\text{Perim}_G$ be the length of the perimeter of the lesion segment in the green channel $L_{green}$. G1 is the length of the lesion segment border normalized by the square root of the area of the lesion segment.

$$G1 = \frac{\text{Perim}_G}{\sqrt{\sum_{x=1}^{Nx}\sum_{y=1}^{Ny}L_{green}}} - \frac{2\pi}{\sqrt{\pi}} \quad (22)$$

B15 is then mean intra-branch coefficient of variation.

$$B15 = \left\langle\frac{\sigma(I_{branch}(\theta))}{\langle I_{branch}(\theta)\rangle}\Big|_{\theta=0}^{\theta=2\pi}\right\rangle \quad (23)$$

The fitting algorithm depicted in FIG. 1 yielded a slope S for the sigmoidal edge fit. R1 was the standard deviation of the slope fit values $$R1=\sigma(S)|_{\theta=0}^{\theta=2\pi} \quad (24)$$

R2 is the fractal dimension of the lesion segment binary image as defined by [30]

$$R2=D(L_{red}(y,x)) \quad (25)$$

Each branch segment in terminated on two ends in either a branch point or an end point. R3 is the connectedness of the pigmented network, defined as the ratio of the number of branch points $N_{BP}$ to the number of endpoints $N_{EP}$.

$$R3 = \frac{N_{BP}}{N_{EP}} \quad (26)$$

R4 is the size of the lesion segment $L_{red}$, which is the sum of the binary mask valued at one inside the lesion segment and zero outside the lesion segment.

$$R4 = \sum_{x=1}^{Nx}\sum_{y=1}^{Ny}L_{red} \quad (27)$$

R5 is the mean slope (S) for the edge fit function $s_e(r)$ (as used in Eq. 13) evaluated only for the fits that did not require more iterations of the fminsearch( ) operator than the 200 allowed.

$$R5=\langle S|_{\theta=0}^{\theta=2\pi}\rangle \quad (28)$$

Let the instantaneous radius of the lesion, as in Eq. 3, be denoted by $R_R(\theta)$ over the angular sweep of $\theta$. R6 is then the coefficient of variation in the lesion radius over the angular sweep $$R6 = \frac{\sigma(R_{red}(\theta)|_{\theta=0}^{\theta=2\pi})}{\langle R_{red}(\theta)|_{\theta=0}^{\theta=2\pi}\rangle} \quad (29)$$

Let $N_b(\theta, d\theta)$ be the number of pigmented network branches identified in a differential angle element $d\theta$ as a function of angle $\theta$ over the angular sweep. R7 is then the range in number of branches detected as a function of angle.

$$R7 = \max(N_{branch}(\theta,d\theta)) - \min(N_{branch}(\theta,d\theta)) \quad (30)$$

R8 is the range in the standard deviation of pixel brightness on the angular sweep arm over the angular sweep.

$$R8 = \max(R_{std}(\theta)|_{\theta=0}^{\theta=2\pi}) - \min(R_{std}(\theta)|_{\theta=0}^{\theta=2\pi}) \quad (31)$$

Pixels with the lesion segment were scored as a set $P_{lesion}$. The coefficient of variation for pixels within the lesion segment was calculated by dividing the standard deviation of intra-lesional pixel brightness by the mean lesional pixel brightness. R9 is then the coefficient of variation in pixel brightness within the lesion.

$$R9 = \frac{\sigma(P_{lesion})}{\langle P_{lesion}\rangle} \quad (32)$$

R10 is the mode error, calculated the same as B4 but evaluated only for the fits that did not exceed the number of fitting iterations (200) allowed.

$$R10 = \mathrm{mode}\left(\sum_{R=0.5D}^{R=1.5D}(P_e(r) - \mathrm{erf}(r))^2\right)\Big|_{\theta=0}^{\theta=2\pi} \quad (33)$$

The maximum asymmetry of the lesion was normalized by the eccentricity of the lesion E as calculated using the stats.Ecentricity function in Matlab. This normalization enabled de-emphasis of uniform ovals as asymmetric. R11 is then the maximum asymmetry of the lesion silhouette:

$$R11 = \max\left(\frac{A}{E}\right) \quad (34)$$

R12 is the sum of the normalized derivative in lesion radius D over the angular sweep:

$$R12 = \sum_{\theta=0}^{\theta=2\pi} \mathrm{abs}(R_{red}(\theta, d\theta) - R_{red}(\theta-1, d\theta)) \quad (35)$$

R13 is the asymmetry of the lesion silhouette evaluated in the standard technique:

$$R13 = A\left|\theta_{sym} - \frac{\pi}{2}\right| \quad (36)$$

Figure 2:
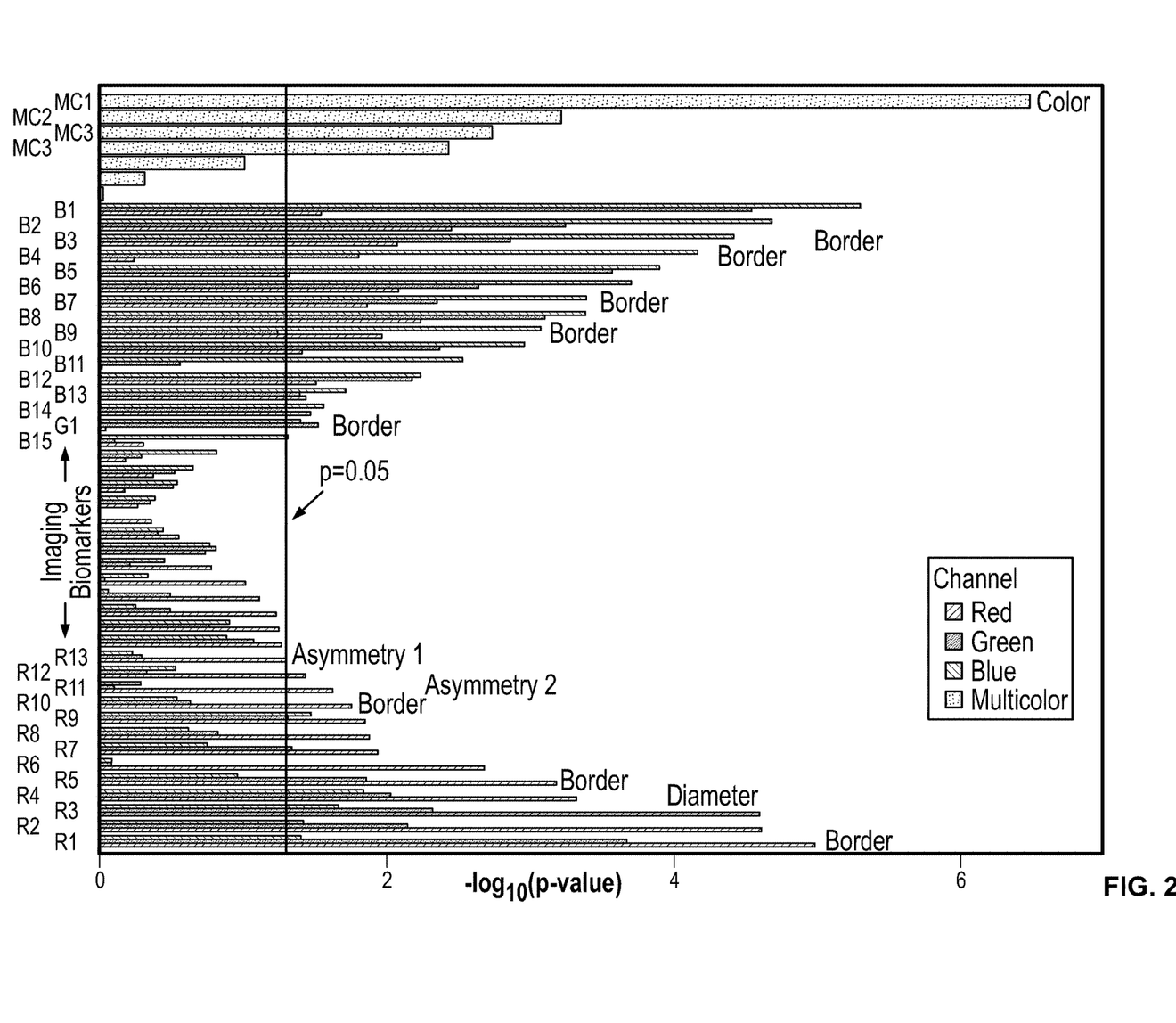
FIG. 2 depicts the MIBs ranked by discriminant significance according to an embodiment of the invention.

FIG. 2 depicts the MIBs ranked by discriminant significance. The melanoma imaging biomarkers (MIBs) with statistical significance for melanoma discrimination (p<0.05, vertical black line) are labeled on the vertical axis describing the color channel they were used in: B1-B14 from the blue channel, G1 from the green channel and R1-R13 from the red channel. MC1-MC4 denotes MIBs that used multiple color channel information. The text to the right of the bars indicates MIBs that contain information based on the dermoscopic ABCD criteria. The most significant MIB was the number of colors identified in the lesion while the Diameter of the lesion had intermediate significance and the asymmetry of the lesion silhouette had borderline significance. The lesion Border features pertain to the edge demarcation.

Figure 3:
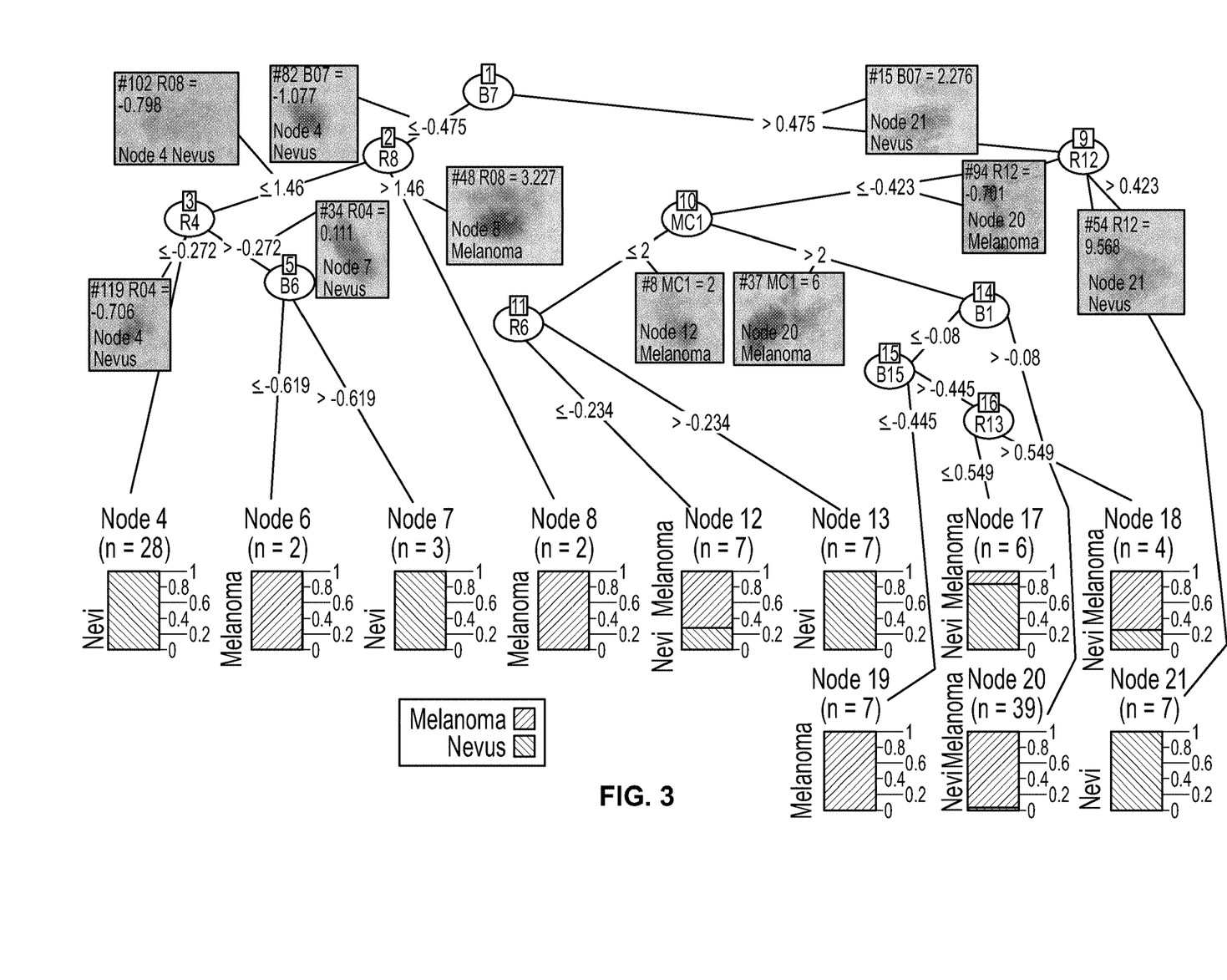
FIG. 3 depicts a decision tree built with the C5.0 algorithm according to an embodiment of the invention.

FIG. 3 depicts a decision tree built with the C5.0 algorithm according to an embodiment of the invention. The algorithm was applied to predict lesions type (melanoma vs. nevus) with the full data set that included 112 lesions and 33 MIBs. The final decision tree has 10 decision nodes (#1, #2, #3, #5, #9, #10, #11, #14, #15, and #16) and 11 terminal nodes (#4, #6, #7, #8, #12, #13, #17, #18, #19, #20 and #21). The algorithm selected decision nodes based on four MIBs from the blue channel (B1, B6, B7, and B15), five MIBs from the red channel (R4, R6, R8, R12, and R13) and one multicolor MIB (MC1). At the terminal nodes the proportion of melanomas (light gray) and nevi (dark gray) are shown with stacked bar plots. The final classification has yielded 7 pure terminal nodes (#4, #6, #7, #8, #13, #19 and #21) where melanoma or nevi have 100% prevalence. The nodes #4 and #20 together have 59.8% of the lesions and they perfectly discriminate nevi and melanoma, respectively.

Median estimates for the performance of IBs according to different channels across all methods is tabulated in Table 3. The sensitivity, specificity, predictive negative value and predictive positive value were evaluated for each one of 500 test sets according to the described 12 methods. The overall median (across methods and test sets) was used to summarize the classification performance.

TABLE 3

| Wavelength | Sensitivity | Specificity | PPV | PNV |
| --- | --- | --- | --- | --- |
| Red | 0.66 | 0.64 | 0.65 | 0.67 |
| Green | 0.64 | 0.69 | 0.67 | 0.64 |
| Blue | 0.71 | 0.69 | 0.72 | 0.69 |
| Best + Multicolor | 0.79 | 0.77 | 0.77 | 0.75 |

Figure 4:
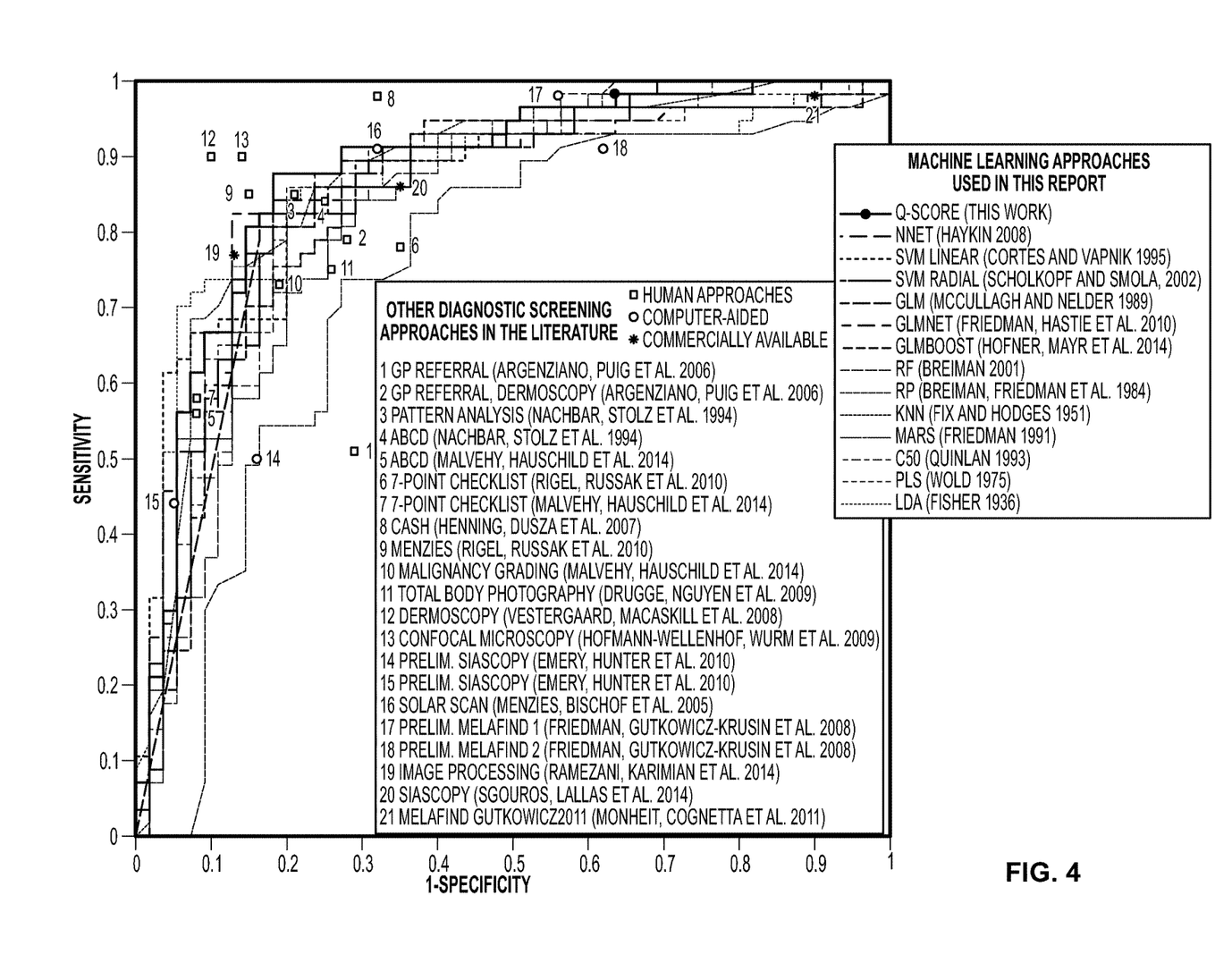
FIG. 4 depicts a Receiver Operator Characteristic ("ROC") Curve demonstrating the sensitivity and selectivity of the Q-Score according to the invention, compared to individual machine learning algorithms, and certain prior art diagnostic methods of melanoma diagnosis.

FIG. 4 depicts a Receiver Operator Characteristic ("ROC") Curve, demonstrating the sensitivity and selectivity of the Q-Score according to the invention. The receiver-operator characteristic curves for the individual machine learning approaches (thin colored lines) are outperformed by the compound melanoma Q-score (thick black line) with clinically relevant sensitivity=98% and specificity=36% (red circle). Data points of comparative approaches from the literature are marked with symbols that indicate their nature (machine or human-derived) and are numbered by the legend references. The machine learning approaches are abbreviated in the legend.

The methods according to the invention may be described as a series of conceptual "steps." As would be apparent to the person of ordinary skill in the art, the steps may be followed sequentially, or in an order different from the order stated;

the steps may be done in parallel, done at the same time, or done iteratively, without departing from the scope of the invention.

The melanoma Q-score diagnostic combined these discrete metrics, using statistics and machine learning. Because the data set consisted of lesion images that were the subject of biopsy to obtain a gold standard comparison, it is unknown if the melanoma Q-score would detect more melanomas than were detected by the screening procedure that led to the decision to biopsy. However, the melanoma Q-score would increase the pretest probability of biopsy, making biopsy, which is invasive, a more cost effective procedure.

A striking result was the natural segregation of metrics: they were either diagnostic in the blue channel of the RGB image or diagnostic in the red channel, but not both. Some standard clinical criteria correlated well with melanoma such as the presence of multiple dermoscopic colors. Others, such as the asymmetry of the lesion border analyzed in the standard manner did not achieve p<0.05 statistical significance. Clinical practice should be guided to evaluate asymmetry not perpendicular to the most symmetric axis but rather on any axis and be excluded if the lesion is a uniform oval. as in metric R10 did, achieving statistical significance.

Though the melanoma Q-score combined information from the red green and blue channel, analysis at single color channels showed the blue channel outperformed the red channel and the red channel outperformed the green channel when single color channels are isolated.

Melanoma color variation represents differing function of a subpopulation of underlying melanocytes that are contained in the lesion. Mutations in genes that control pigmentation lead to atypical colors such as red, blue and no color at all (e.g., regression).

A sweeping arm is a line segment connecting the center of the lesion to the border. The "clock-like" sweep as used herein, means rotating the sweeping arm about the fixed center of the image in either a clockwise or counter-clockwise direction to obtain information about the pixels on the sweeping arm as a function of rotation angle. The lesion's center may be determined by a number of known methods, for example, as described in the aforesaid U.S. patent application Ser. No. 14/051,053 (Patent Application Publication 2015/0025343) and Ser. No. 14/907,208 (Patent Application Publication 2016/0166194). To obtain metrics from the image data, the sweeping arm rotates around the center with one end fixed at the center for 2 pi ($2\pi$) radians or 360° (one complete sweep). Data is sampled at pixels along the sweeping arm, and at regular angular intervals of radians or degrees. The data obtained in the sweep may be processed into a series of metrics and/or one or more classifiers which cannot be obtained by evaluation of image data which have not been transformed into polar coordinates.

The imaging biometrics enable quantitative analysis of parameters familiar from conventional dermatological examination, such as the ABCD technique of lesion screening, which evaluates the asymmetry (A) of a lesion, and lesion border (B), color (C) and dermoscopic structures (D). But the systems and methods of the invention also provide a wealth of information that cannot be obtained from conventional screening, ultimately yielding a percent likelihood that a lesion is melanoma or nevus, which conventional screening could never do. According to the invention, the factors relevant to conventional dermatology are synthesized in a series of imaging biomarkers, which are then combined in one or more classifiers that may be trained on a set of lesions of known pathology to yield a system of diagnosis of skin disease embodied in a Q-Score.

The foregoing description of the preferred embodiments is for illustration and is not to be deemed as limiting the invention defined by the following claims. The primary application of the invention is to detect melanoma in humans and to distinguish cancerous from non-cancerous lesions. However, in principle, the apparatus and methods have broad application in the detection and display of other skin diseases and diseases in other human tissues. Moreover, using the clock sweep method of analyzing multispectral image data according to the invention lends itself to the development of improved metrics and more discriminating classifiers for the detection of melanoma, without departing from the scope of the invention. The foregoing descriptions of a clinical apparatus and cellular phone apparatus enable the person of ordinary skill to practice variants thereof without departing from the scope of the invention.

What is claimed is:

1. An apparatus for obtaining an indication of a likelihood of the presence or absence of skin disease in a lesion on a subject's skin, comprising:
    an illumination system adapted to illuminate the subject's skin, including the lesion;
    a camera adapted to obtain image data in at least RGB channels from light reflected from the subject's skin;
    a computer processor adapted process the image data and to implement a clock-like sweep algorithm to obtain imaging biomarkers, including at least a set of single-color-channel (SCC) imaging biomarkers extracted from single color channels and a set of Multi-Color (MC) imaging biomarkers extracted from the RGB color channels by characterizing differences in lesion features between the RGB color channels and combining said set of SCC imaging biomarkers and set of MC biomarkers into at least one classifier; and
    a display adapted to display the likelihood of the presence or absence of skin disease in the lesion on the subject's skin based on an output of said classifier.

2. The apparatus according to claim 1, wherein the computer processor is adapted to extract three versions of at least one of the set of SCC imaging biomarkers for the lesion, one from each color channel.

3. The apparatus according to claim 1, wherein said processor, in performing the clock-like sweep algorithm: (1) creates a sweeping arm extending out from a center of the lesion, (2) rotates the sweeping arm about the center in angular increments, (3) at a plurality of said angular increments, samples the image data at a plurality of pixels along the sweeping arm, and (4) processes said image data samples to obtain imaging biomarkers.

4. A method for obtaining an indication of a likelihood of the presence or absence of skin disease in a lesion on a subject's skin, comprising the steps of:
    illuminating the subject's skin including the lesion;
    obtaining image data in at least RGB channels from light reflected from the subject's skin with a camera;
    processing the image data with a computer processor adapted to implement a clock-like sweep algorithm to obtain metrics and/or one or more classifiers defining the rotational symmetry of the lesion, including at least a set of single-color-channel (SCC) metrics extracted from single color channels and a set of Multi-Color (MC) metrics extracted from the RGB color channels by characterizing differences in lesion features between the RGB color channels, and combining said set of SCC imaging biomarkers and set of MC biomarkers into at least one classifier; and displaying the indication of the likelihood of the presence or absence of skin disease in the lesion on the subject's skin based on an output of said classifier.

5. The method according to claim 4, including extracting three versions of at least one of the set of SCC imaging biomarkers for the lesion, one from each color channel.

6. An apparatus for detecting skin disease in a lesion on a subject's skin, comprising: a mechanical fixture having a flat surface to position or press against the subject's skin to define a distal imaging plane containing said lesion; a camera adapted to obtain image data from light reflected from said distal imaging plane; a processor adapted to process the image data with a clock-like sweep algorithm to obtain metrics and/or one or more classifiers defining the rotational symmetry of the lesion; and an output device that indicates a likelihood of the presence or absence of skin disease in the subject from the metrics and/or one or more classifiers; wherein the processor is adapted to transform the image data into at least one classifier, the at least one classifier including total number of colors in the lesion (MC1), and further including at least one additional imaging biomarker selected from the group consisting of:

normalized difference in lesion size between the red and blue color channels (MC2);

mean coefficient of variation of lesion radii among the color channels (MC3);

binary presence of blue-gray or white in the image (MC4);

average of the absolute value of the derivative of $R_m(\theta)$ over the angular sweep is the mean instantaneous brightness shift from one angular analysis position to the next over the entire 360-degree angular range (B1);

variance over the angular sweep of the variance in pixel brightness over the radial sampling arm (B2);

mean error between a model $s_e(r)$ and image data $p_e(r)$ evaluated over a range equal to the distance between the center and the lesion border but centered on the edge of the lesion (B3);

mode error in the blue channel (B4);

standard deviation of the set of derivative values of the mean brightness (B5);

normalized inter-branch pixel intensity variation (B8);

standard deviation of error (B9);

normalized angular coefficient of brightness variation (B10);

standardized variance of branch lengths (B11);

normalized range of angular brightness (B12);

mean intra-branch coefficient of variation (B15);

standard deviation of sigmoidal edge fit slope values (R1);

fractal dimension of the lesion segment binary image (R2);

connectedness of the pigmented network (R3);

size of the lesion segment (R4);

mean slope for an edge fit function $s_e(r)$ (R5);

coefficient of variation in the lesion radius over the angular sweep (R6);

range in number of branches detected as a function of angle (R7);

range in a standard deviation of pixel brightness on the angular sweep arm over the angular sweep (R8);

coefficient of variation in pixel brightness within the lesion (R9);

mode error in the red channel (R10);

maximum asymmetry of the lesion silhouette (R11);

sum of the normalized derivative in lesion radius D over the angular sweep (R12); and asymmetry of the lesion silhouette (R13).

7. The apparatus according to claim 6, wherein said processor, in performing the clock-like sweep algorithm: (1) creates a sweeping arm extending out from a center of the lesion, (2) rotates the sweeping arm about the center in angular increments, (3) at a plurality of said angular increments, samples the image data at a plurality of pixels along the sweeping arm, and (4) processes said image data samples to obtain imaging biomarkers.

8. A method for detecting skin disease in a lesion on a subject's skin, comprising: positioning a mechanical fixture having a flat surface against the subject's skin to define a distal imaging plane containing said lesion; obtaining image data with a camera from light reflected from said distal imaging plane; processing the image data with a clock-like sweep algorithm to obtain imaging biomarkers; and outputting a likelihood of the presence or absence of skin disease in the subject from the imaging biomarkers; wherein the processor is adapted to transform the image data into at least one classifier, the classifier including at least total number of colors in the lesion (MC1), and further including at least one additional imaging biomarker selected from the group consisting of:

normalized difference in lesion size between the red and blue color channels (MC2);

mean coefficient of variation of lesion radii among the color channels (MC3);

binary presence of blue-gray or white in the image (MC4);

average of the absolute value of the derivative of $R_m(\theta)$ over the angular sweep is the mean instantaneous brightness shift from one angular analysis position to the next over the entire 360-degree angular range (B1);

variance over the angular sweep of the variance in pixel brightness over the radial sampling arm (B2);

mean error between a model $s_e(r)$ and image data $p_e(r)$ evaluated over a range equal to the distance between the center and the lesion border but centered on the edge of the lesion (B3);

mode error in the blue channel (B4);

standard deviation of the set of derivative values of the mean brightness (B5);

normalized inter-branch pixel intensity variation (B8);

standard deviation of error (B9);

normalized angular coefficient of brightness variation (B10);

standardized variance of branch lengths (B11);

normalized range of angular brightness (B12);

mean intra-branch coefficient of variation (B15);

standard deviation of sigmoidal edge fit slope values (R1);

fractal dimension of the lesion segment binary image (R2);

connectedness of the pigmented network (R3);

size of the lesion segment (R4);

mean slope for an edge fit function $s_e(r)$ (R5);

coefficient of variation in the lesion radius over the angular sweep (R6);

range in number of branches detected as a function of angle (R7);

range in a standard deviation of pixel brightness on the angular sweep arm over the angular sweep (R8);

coefficient of variation in pixel brightness within the lesion (R9);

mode error in the red channel (R10);

maximum asymmetry of the lesion silhouette (R11);

sum of the normalized derivative in lesion radius D over the angular sweep (R12); and asymmetry of the lesion silhouette (R13).

9. The method according to claim 8, wherein a plurality of said imaging biomarkers are included in a plurality of classifiers, and further comprising generating a Q-Score probability of melanoma by evaluating a function of probability across K available classifiers:

$$Qscore = \text{median}\{Prob_i(Melanoma|M)\}; i=1,2,\ldots,k$$

where $Prob_i \in \{0,1\}$ is the probability of the lesion being a melanoma, as predicted by the i-th classifier based on a set of MIBs M.

10. The method according to claim 9, wherein said Q-Score is generated from a test set of skin lesions having known pathology.

11. An apparatus for obtaining an indication of a likelihood of the presence or absence of skin disease in a lesion on a subject's skin, comprising:

an illumination system adapted to illuminate the subject's skin, including the lesion;

a camera adapted to obtain image data in at least RGB channels from light fluoresced from the subject's skin;

a computer processor adapted process the image data and to implement a clock-like sweep algorithm to obtain imaging biomarkers, including at least a set of single-color-channel (SCC) metrics extracted from single color channels and a set of Multi-Color (MC) metrics extracted from the RGB color channels by characterizing differences in lesion features between the RGB color channels; and extracting three versions of each SCC metric for the lesion, one from each color channel, and combining said set of SCC imaging biomarkers and set of MC biomarkers into at least one classifier; and a display adapted to display the likelihood of the presence or absence of skin disease in the lesion on the subject's skin based on an output of said classifier.

12. The apparatus according to claim 11, wherein the camera is adapted to obtain an image of the lesion having specific or non-specific targets thereon labeled with a fluorescent label.

13. An apparatus for obtaining an indication of a likelihood of the presence or absence of skin disease in a lesion on a subject's skin, comprising:

an illumination system adapted to illuminate the subject's skin, including the lesion;

a camera adapted to obtain image data in at least RGB channels from light reflected from the subject's skin;

a computer processor adapted process the image data and to implement a clock-like sweep algorithm to obtain imaging biomarkers, including, in said channels: (1) creating a sweeping arm extending out from a center of the lesion, (2) rotating the sweeping arm about the center in angular increments; (3) sampling pixel brightness data at a plurality of pixels along the sweeping arm at said angular increments; (4) processing said pixel brightness data to obtain at least a set of single-color-channel (SCC) imaging biomarkers extracted from single color channels and a set of Multi-Color (MC) imaging biomarkers extracted from the RGB color channels by characterizing differences in lesion features between the RGB color channels; and (5) combining said SCC imaging biomarkers and MC biomarkers into at least one classifier; and a display adapted to display the likelihood of the presence or absence of skin disease in the lesion on the subject's skin.

* * * * *